United States Patent [19]

Zeljko et al.

[11] Patent Number: 5,239,087
[45] Date of Patent: Aug. 24, 1993

[54] PROCESS FOR THE PRODUCTION OF DIPOTASSIUM-ASCORBATE-2-SULFATE

[75] Inventors: Guberovic Zeljko, Koprivnica; Marijan Hohnjec, Zagreb; Josip Kuftinec, Hrvatski/Leskovak; Milan Oklobdzija, Zagreb, all of Yugoslavia

[73] Assignee: Enco Engineering Chur AG, Chur, Switzerland

[21] Appl. No.: 553,788

[22] Filed: Jul. 17, 1990

[30] Foreign Application Priority Data

Jul. 17, 1989 [CH] Switzerland .................. 2673/89

[51] Int. Cl.$^5$ .................................. C07D 307/62
[52] U.S. Cl. ................................................ 549/317
[58] Field of Search ..................... 549/315, 210, 317

[56] References Cited

U.S. PATENT DOCUMENTS

| | | | |
|---|---|---|---|
| 3,954,809 | 5/1976 | Deyoe et al. | 549/210 |
| 4,070,377 | 1/1978 | Hayashi et al. | 549/317 |
| 4,071,534 | 1/1978 | Hayashi et al. | 549/317 |

FOREIGN PATENT DOCUMENTS 2452719  11/1973  Fed. Rep. of Germany .

OTHER PUBLICATIONS

Journal of the Chemical Society, "Synthesis and Stability of L-ascorpate 2-sulphate", pp. 1220–1224, 1974.
Chemical Abstracts, No. 10, Sep. 5, 1977, vol. 87, p. 338 No. 73386m.

*Primary Examiner*—C. Warren Ivy
*Assistant Examiner*—A. A. Owens
*Attorney, Agent, or Firm*—Tarolli, Sundheim & Covell

[57] ABSTRACT

The present invention relates to a process for the production of dipotassium-ascorbate-2-sulfate-dihydrate, a vitamin C derivative. It is used, among other things, as an additive to fish feed. In the process according to the process according to the invention, trimethylamine-sulfur-trioxide complex is added in only slight molar excess to a concentrated solution of potassium-L-ascorbate in water, and the pH value of this reaction mixture is set by successive additions of potassium hydroxide at a value in the range between 9.5 and 10.5, and is kept at this value for the duration of the reaction. The process permits the profitable production of dipotassium-ascorbate-2-sulfate-dihydrate on a large industrial scale. It is also explained how trimethylamine-sulfur-trioxide complex can be recovered from trimethylamine which occurs as a by-product during the production of dipotassium-ascorbate-2-sulfate.

14 Claims, No Drawings

PROCESS FOR THE PRODUCTION OF DIPOTASSIUM-ASCORBATE-2-SULFATE

TECHNICAL FIELD

This invention relates to a process for the production of dipotassium-ascorbate-2-sulfate of the formula

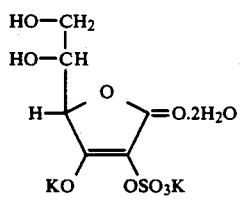

Dipotassium-ascorbate-2-sulfate (or the corresponding dihydrate) is a vitamin C derivative which, however, is more stable than vitamin C itself. It is used, among others, as an additive to fish feed (A. K. Soliman, K. Jauncey, R. J. Roberts; Aquaculture 60, 73 (1987)). It is a metabolic product of vitamin C and is formed in fish as a vitamin C reserve. A lack of vitamin C leads to the deficiency disease scurvy. Fish such as salmon, for example, have the enzyme (sulfatase) necessary for splitting off the sulfate radical, whereby their organism can form back the pure vitamin from the derivative stored.

STATE OF THE ART

From P. A. Sieb et al, J. Chem. Soc. Perkin I, 1120, (1974) is known the production of ascorbic acid, sulfated in Position 2 by the reaction of ascorbic acid and protected in positions 5 and 6 with pyridine-sulfur-trioxide complex in a dimethyl formamide solution.

From U.S. application Ser. No. 3,954,809 is known the production of L-ascorbate-2-sulfate, even from unprotected ascorbic acid or its salts, through reaction with trimethylamine-sulfur-trioxide complex in aqueous solution and in the presence of a sufficient amount of a free base, especially sodium hydroxide, at a pH value from 10 to 10.5. Through the presence of the free base, the negative charge of the oxygen atom in position 3 is moved to the oxygen atom in position 2, whereby this latter becomes reactive and selectively sulfated. In the known process, a very dilute solution is used (ascorbic acid concentration about 80 grams per liter). To reach completion of the sulfating reaction, the trimethyl amine-sulfur-trioxide complex is added in quite a great excess (over 50%). However, through hydrolysis of this excess of sulfur complex, there results in parallel a considerable amount of inorganic sulfate. For reasons of purity, this cannot be left in the end product The same applies to the trimethylamine resulting in the reaction and in solution, as well as the unreacted complex still present. The separation of the trimethylamine takes place in the known process by raising the pH value to about 12.5 and then evaporating, or by conducting the reaction mixture through a column with a cation exchanger resin. The separation of the inorganic sulfate takes place, by adding barium hydroxide, as barium sulfate. After adding methanol and filtering, there is obtained finally barium-ascorbate-2-sulfate in crystalline form. However, this barium salt is toxic to fish. For use in fish feed, this would have to be converted into the far more suitable potassium salt. This is possible in principle by adding $K_2SO_4$ to a solution of the barium salt obtained in water, separating the barium sulfate formed by filtration, and final evaporation of the filtrate. Another possibility, described by B. M. Tolbert et al, in ANN. N.Y. ACAD. SCI. (1975/. 258, 48-69, consists of converting the barium-ascorbate-2-sulfate into the corresponding dipotassium salt by conducting an aqueous solution of the barium-ascorbate2-sulfate through a column containing DOWEX 50-K+.

By the process just described, it is true dipotassium-ascorbate-2-sulfate-dihydrate can be produced in very high purity. But, especially in view of the very expensive cleansing of the end product, the production of this product for use as additive to fish feed on a big industrial scale by the known process is not feasible because it is much too unprofitable.

Moreover, in the known process, with the necessary addition in portions of the sulfur reagent, a contamination of the environment with trimethylamine would be difficult to prevent.

DESCRIPTION OF THE INVENTION

It is the problem, in particular, of the present invention to provide a process for the production of dipotassium-ascorbate-2-sulfate-dihydrate pure enough for fish feed, which can be carried out with high yield and profitably on a large industrial scale. Moreover, it should be possible to prevent a contamination of the environment with trimethylamine-sulfur-trioxide complex.

The problems mentioned and others are solved according to the present invention through a process as distinguished in claim 1. Advantageous embodiments of this invention are distinguished in the dependent claims.

Accordingly, in the process according to the invention, trimethylamine-sulfur-trioxide complex is added in only slight molar excess to a concentrated solution of potassium-L-ascorbate in water, and the pH value of this reaction mixture is set by successive additions of potassium hydroxide at a value in the range between 9.5 and 10.5 and is kept at this value for the duration of the reaction.

Through the use of a concentrated potassium ascorbate solution, the important advantage is provided that the trimethylamine, easily soluble in water, already escapes during the reaction. Therefore, it does not remains in solution, as in the known process, and thus need not be expensively separated. Moreover, through the high concentration, there is provided a high production capacity and an ideal use of the plant.

Because of the only slight molar excess in which the trimethylamine-sulfur-trioxide complex is added to the concentrated solution of potassium-L-ascorbate, there remains at the end of the reaction time practically no unreacted complex in the reaction mixture. Also, inorganic sulfates cannot form parallel in great amounts. After the trimethylamine has disappeared, the desired end product can be crystallized out directly simply by adding an alkanol, especially ethanol. Most of the inorganic sulfate remains at once in solution. In the end product, there can always be demonstrated 1 to 2% of the inorganic sulfate which, in view of the intended use of the end product as an additive to fish feed, presents no problem. Thus, in the process according to the invention as compared with the known process described above, there is eliminated the separate separation of trimethylamine, the separation of inorganic sulfate, and finally,, the conversion of the toxic barium salt to the desired potassium salt. This latter occurs because of the use of potassium-L-ascorbate in aqueous solution as starting material, and the setting of the pH value in the basic range by means of potassium hydroxide.

The setting of the pH value to a value of 10 for the duration of the reaction takes place in the present invention for the same reason as in the above-mentioned process, to sulfate selectively the oxygen atom in position 2.

Preferably, the concentration of the solution potassium ascorbate in water is set at a value in the range between 500 and 700 grams per liter.

The molar excess in which the trimethyl amine-sulfur-trioxide complex is added to the aqueous potassium ascorbate solution should be not more than 8%, and preferably only 6%.

The temperature of the reaction mixture is preferably set at a value within the range between 57 degrees C. and 65 degrees C., and also, preferably, should be increased in linear fashion from the lower value to the upper value, this latter being with a view to the recovery of the escaping trimethylamine, to be mentioned later.

The whole amount of trimethylamine-sulfur-trioxide complex may be added to the aqueous potassium ascorbate solution right at the beginning of the reaction.

Instead of starting with potassium-L ascorbate, the concentrated solution of potassium ascorbate in water may also be prepared, with advantage, by mixing L-ascorbic acid with water and neutralizing this mixture with potassium hydroxide. For protection of the ascorbic acid, the temperature should here be kept to a value below 25 degrees C.

As already mentioned above, the trimethylamine escaping from the reaction mixture during the reaction can be recovered. For this purpose, it is preferably absorbed in a chlorinated organic solvent, especially in 1,2-dichloroethane, chloroform, carbon tetrachloride or methylene chloride (dichloromethane). This can take place in an absorption column connected with the reaction vessel used, in which the absorption agent circulates well cooled Through this cooling, the temperature of the absorption agent should be kept below about 0 degrees C. The setting of the temperature of the reaction mixture in the reaction vessel at first to only 57 degrees C. and then rising to 65 degrees C. is advantageous because in this way, too strong a development of trimethylamine, possibly exceeding the capacity of the absorption column, at the beginning of reaction is prevented.

With the use of the above absorbant or solvent for the escaping trimethylamine, it is possible to prepare again from the solution obtained the trimethyl amine-sulfur-trioxide complex necessary as reagent for the present process. An especially suitable process, which can be carried out profitably on a large industrial scale, consists of adding chlorosulfonic acid to the solution containing trimethylamine and conducting gaseous ammonia through this reaction mixture in order to recover amine from the amine hydrochloride resulting first as a by-product. The recovery of the amine by means of ammonia is possible because ammonium hydrochloride has a better solubility than ammonium chloride. The amine recovered reacts with chlorosulfonic acid still present to the desired $R_3N:SO_3$ complex.

The resultant ammonium chloride can be dissolved by adding water and stirring. The desired tertiary amine-sulfur-trioxide complex can finally be separated by filtration, washed, and after drying, be obtained as dry end product. During the reaction, the temperature is preferably set at a value between 0 and 30 degrees C. Ammonia is conducted into the reaction mixture at least until its pH value is alkaline.

WAYS OF CARRYING OUT THE INVENTION

The invention will be explained below from a few examples of execution.

EXAMPLE 1

To a mixture of 500 gr (2.84 mol) ascorbic acid and 300 ml water is added a first portion of a solution of 339 g (6 mol) potassium hydroxide in 530 ml water with stirring and cooling to a temperature below 25 degrees C. until a pH value of 8.5 is reached Then 420 grams trimethylamine-sulfur-trioxide complex (3 mol) are added to the resultant potassium ascorbate solution. In an absorber system which is connected with the reaction vessel containing the solution, 2000 ml dichloromethane are circulated and cooled to −10 degrees C. Care is taken that the temperature in the absorber does not rise above about 0 degrees C. Now the temperature in the reaction vessel is raised to 57 degrees C. The pH is set to a value of 10 by adding another portion of the potassium hydroxide solution. The sulfating reaction which then takes place requires about two hours. During this time, the pH value is kept to the above-mentioned value by adding the remaining part of the potassium hydroxide solution, and the temperature is slowly raised to 65 degrees C. The reaction is complete when all the potassium hydroxide solution has been added.

The reaction mixture in the reaction vessel is now cooled to 15 degrees C. Then 2300 ml ethanol (96%) are added for a duration of three hours. At the same time, the temperature is lowered to 5 degrees C. The suspension forming through the crystallizing-out of the desired end portion is stirred for another hour before it is filtered. The filter residue containing the desired end product in crystal form is washed again with 1400 ml ethanol (70%).

In a test experiment in the manner described above, it was possible to obtain 960 grams of dry dipotassium-ascorbate-2-sulfate as a white powder with a melting point of 150–152 degrees C. corresponding to a yield of 92%. The purity of the product could be determined at 98.6% (HPLC analysis).

In the same test experiment after the reaction, there could be demonstrated in the dichloromethane circulating in the absorber system 143 grams absorbed trimethylamine corresponding to 85% of the theoretic value.

An example is given below of how trimethylamine-sulfur-trioxide complex can be recovered from a solution of trimethylamine in dichloromethane in a separate process.

33.5 ml (0.507 mol) chlorosulfonic acid are added slowly to an ice-cooled and well-stirred solution of 28.5 g (0.5 mol) trimethylamine in 150 ml dichloromethane. The temperature is kept at a value below 20 degrees C. The first half of the chlorosulfonic acid reacts very exothermically and should therefore be added very slowly, while the second half requires less care. After all the chlorosulfonic acid has been added, gaseous ammonia is conducted through the solution until a basic value of pH is reached. 80 ml water are added with vigorous stirring to the resultant suspension. After 15 minutes, the solid product is filtered out, washed three times with 25 ml water in each case, and then dried.

In the manner described, it should be possible to produce 55.5 to 66.5 grams corresponding to a yield of 80 to 94% of dry end product. (Trimethylamine-sulfurtrioxide complex).

EXAMPLE 2

1500 ml of the reaction mixture in Example 1 are cooled to 0 degrees C. after the end of reaction (also carried out as in Example 1). Seed crystals of pure dipotassium-ascorbate-2-sulfate are added, and the mixture is stirred for three hours. The crystals which have formed during this time are separated by filtration, washed with 500 ml ethanol (70%), and dried at 60 degrees C. under reduced pressure.

In a test experiment, there could be obtained in this way 640 grams (61%) dry end product with a purity of 99.83%. (HPLC analysis).

Then the mother fluid is concentrated under reduced pressure to 400 ml, and the temperature is lowered to 5 degrees C. 400 ml ethanol (96%) are added successively over a period of two hours with constant stirring.

In the test experiment, there could be obtained in this way 310 grams (30%) more of the desired end product with a purity of 97.8% (HPLC analysis).

We claim:

1. Process for the production of dipotassium-ascorbate-2-sulfate, of the formula $$\begin{array}{c} HO-CH_2 \\ | \\ HO-CH \\ \quad\diagdown \\ H-\!\!\!\diagup\!\!\!\!\diagdown\!\!\!\!=\!\!O\!\cdot\!2H_2O \\ \quad\diagup\!\!\!\!=\!\!\!\!\diagdown \\ KO \quad OSO_3K \end{array}$$

in which trimethylamine-sulfur-trioxide complex is added in only slight molar excess, not more than eight molar precent excess, to a concentrated solution of potassium ascorbate in water, and the pH vale of this reaction mixture is set by the successive addition of potassium hydroxide to a value in the range between 9.5 and 10.5, and kept at this value for the duration of the reaction.

2. Process according to claim 1, with the distinction that the pH value is set to a value of 10 and kept at this value for the duration of the reaction.

3. Process according to claim 1, with the distinction that the concentration of the solution of potassium ascorbate in water is set at a value in the range between 500 and 750 grams per liter.

4. Process according to claim 1, with the distinction that the temperature of the reaction mixture is set to a value in the range between 57 and 65 degrees C., and is raised during the course of reaction from the lower to the upper value.

5. Process according to claim 1, with the distinction that the whole amount of trimethylamine-sulfur-triox-ide complex is added to the aqueous potassium ascorbate solution at the same time.

6. Process according to claim 1, with the distinction that the concentrated solution of potassium ascorbate in water is prepared by mixing L-ascorbic acid with water and neutralizing this mixture with potassium hydroxide.

7. Process according to claim 6, with the distinction that the temperature in the production of the concentrated potassium ascorbate solution is kept at a value below 25 degrees C.

8. Process for the production of dipotassium-ascorbate-2-sulfate, of the formula $$\begin{array}{c} HO-CH_2 \\ | \\ HO-CH \\ \quad\diagdown \\ H-\!\!\!\diagup\!\!\!\!\diagdown\!\!\!\!=\!\!O\!\cdot\!2H_2O \\ \quad\diagup\!\!\!\!=\!\!\!\!\diagdown \\ KO \quad OSO_3K \end{array}$$

in which trimethylamine-sulfur-trioxide complex is added in only slight molar excess, to a concentrated solution of potassium ascorbate in water, and the pH value of this reaction mixture is set by the successive addition of potassium hydroxide to a value in the range between 9.5 and 10.5, and kept at this value for the duration of the reaction, with the distinction that the trimethylamine escaping from the reaction mixture during the reaction is absorbed in a chlorinated organic solvent.

9. Process according to claim 8, with the distinction that from the trimethylamine absorbed in the chlorinated organic solvent, tertiary amine-sulfur-trioxide complex is recovered by adding chlorosulfonic acid to the solution and conducting gaseous ammonia in the reaction mixture so obtained in order to recover amine from the amine hydrochloride resulting first as a by-product.

10. Process according to claim 1, with the distinction that ammonia is conducted in the reaction mixture at least until its pH value is alkaline.

11. Process according to claim 1 with the distinction that the molar excess, in which the trimethylamine-sulfur-trioxide complex is added to the aqueous potassium ascorbate solution, is not more than 6%.

12. Process according to claim 1 with the distinction that an alkanol is added to the reaction mixture and dipotassium ascorbate-2-sulfate-dihydrate crystals resulting from the addition are separated from the reaction mixture.

13. Process according to claim 12 wherein said alkanol is selected from the group consisting of methanol or ethanol.

14. Process according to claim 8 wherein said chlorinated organic solvent is selected from the group consisting of 1,2-dichloroethane, chloroform, carbon tetrachloride, and methylene chloride.

* * * * *